United States Patent [19]
Smith et al.

[11] Patent Number: 5,939,279
[45] Date of Patent: Aug. 17, 1999

[54] INHIBITION OF BACTERIAL BINDING BY HIGH-MANNOSE OLIGOSACCHARIDES

[75] Inventors: Sam Smith; Alan D. Elbein; Y. T. Pan, all of Little Rock, Ark.

[73] Assignee: The Board of Trustees of the University of Arkansas, Little Rock, Ark.

[21] Appl. No.: 08/932,876

[22] Filed: Sep. 18, 1997

[51] Int. Cl.⁶ .................. G01N 33/554; G01N 33/53; C12Q 1/18
[52] U.S. Cl. .................. 435/7.32; 435/7.2; 435/32
[58] Field of Search .................. 435/32, 7.2, 7.32

[56] References Cited

PUBLICATIONS

Wold et al., "Secretory Immunoglobulin A carries oligosaccharide receptors for *E. coli* typy 1 fimbrial lectin", Infection and Immunity, Sep. 1990, vol. 58, No. 9 pp. 3073–3077.
Firon et al., "Interaction of manose–containing oligosaccharides with the fimbrial lectin of *E. coli*", Biochem Biophys. Res. Commun., 1982, 105, pp. 1426–1432.
Jones et al. "FimH adhesin of type I pili is assembled into a fibrillar tip structure in the Enterobacteriaceae", Proc. Natl. Acad. Sci. USA, Mar. 1995, vol. 92, pp. 2081–2085.
Elbein et al., "Glycosidase inhibitors: inhibitors of N–linked oligosaccharide processing", FASEB, Dec. 1991, vol. 5, pp. 3055–3063.
Eden et al., "Inhibition of Bacterial Attachment", Current Topics in Microbiology, 1990, vol. 151, pp. 167–183.

*Primary Examiner*—Sandra E. Saucier
*Assistant Examiner*—Vera Afremova
*Attorney, Agent, or Firm*—Benjamin Aaron Adler

[57] ABSTRACT

The present invention describes a method for the treatment of gram-negative bacterial infections using high-mannose containing oligosaccharides. Specifically the use of $Man_9$ $(GlcNAc)_2$-hydrophobic glycopeptides (i.e. tyrosinamide) to block adhesion of the bacteria pili to the oligosaccharide of the host cells plasma membrane in infections of *Enterobacter cloacae* and other Enterobacter and gram-negative species.

8 Claims, 10 Drawing Sheets

| Structures of Oligosaccharide Added | Concentration (μM) | Adherence CPM | Adherence % of Control |
|---|---|---|---|
| None | - | 1,161 | 100 |
| Man | 25 | 1,329 | 114 |
| αMe-Man | 25 | 1,019 | 88 |
| Manα1→3Man | 25 | 1,334 | 115 |
| Manα1→6Man | 25 | 1,008 | 87 |
| Manα1→6<br>　　　Man<br>Manα1→3 | 25 | 1,006 | 87 |
| Manα1→6<br>　Manα1→6<br>　　　　　Man<br>　Manα1→3<br>Manα1→3 | 25 | 928 | 80 |

FIGURE 3-1

Enterobacter cloacae:  DISYDLSNVFNSSNNK
                       || |||| || | ||
Salmonella typhimurium: 34 DIFYDLSDVFTSGNNQ 49

Enterobacter cloacae:  IPFRLDDSAQAQVGIRVWPVSITGNK
                       ||| ||| | | |||| || | || |
Salmonella typhimirium: 293 IPFHLDDNAAARVGIRAWPISVTGIK 318

Enterobacter cloacae:  AEGRFTSRGYLRVDY
                       ||| || | |||||||
Salmonella typhimirium: 320 AEGPFTARGYLRVDY 334

FIGURE 6

INHIBITION OF BACTERIAL BINDING BY HIGH-MANNOSE OLIGOSACCHARIDES

BACKGROUND OF THE INVENTION

Federal Funding Legend

This invention was produced in part using funds obtained through grant DK 21800 from the National Institutes of Health. Consequently, the federal government has certain rights in this invention.

1. Field of the Invention

The present invention relates generally to the fields of microbiology and anti-bacterial therapy. More specifically, the present invention relates to high-mannose oligosaccharides that inhibit the binding of gram-negative pathogenic bacteria to cell membranes and uses thereof.

2. Description of the Related Art

Enterobacter species are a major problem to clinicians because of their resistance to multiple drugs, including the new cephalosporins and penicillins (15), and since 1993, the incidence of these organisms in intensive care units has increased. *Enterobacter cloacae* is the species most frequently isolated from clinical specimens, followed by *Enterobacter aerogenes* and *Enterobacter agglomerans* (1,10,11,17). This alarming increase in multiple antibiotic resistant organisms suggests that new chemotherapeutic strategies, such as inhibition of bacterial adhesion, are necessary to control colonization or infection in infants and patients at high risk.

Bacterial attachment to mucosal surfaces is the first step in colonization and pathogenesis (2). A number of bacteria bind to host cell surfaces via a protein to carbohydrate interaction (29). Usually in these cases, the carbohydrate molecule exists as a glycolipid or glycoprotein in the plasma membrane of the host cell, and this "oligosaccharide" is recognized by proteins, called lectins, on the bacterial surface. These lectins are frequently part of the pili or fimbriae that are produced by many bacteria, especially gram-negative organisms (27).

A number of studies have investigated the interaction of enteric bacteria with various animal cells, and have shown that in many cases this binding involves recognition of mannose-containing structures on the animal cell surface by type 1 pili on the bacteria (8,9,26,27,28,29). However, the specific carbohydrate structure that is recognized by type 1 pili has either not been well defined, or varies depending on the source of the type 1 pili. Based on the ability of various mannosides to inhibit the agglutination of yeast by enteric bacteria, Firon, et al (9) concluded that the fimbrial lectins of various genera exhibit differences in sugar specificity, but all strains within a genera exhibit the same sugar specificity.

Studies by Firon et al (8) indicated that aromatic α-glycosides of mannose were more effective as inhibitors of *Escherichia coli* binding to epithelial cells than was α-methylmannoside. In fact, these workers demonstrated that p-nitrophenyl-α-D-mannoside was considerably better as an inhibitor than was α-methylmannoside, and methylumbelliferyl-α-mannoside was even better then the p-nitrophenyl-derivative.

There is a considerable amount of information concerning the structure of type 1 pili (16), and the type 1 fimbrial gene cluster of *Escherichia coli* (18,30) and *Klebsiella pneumoniae* (3) have been cloned. Mutant bacteria lacking the receptor binding function were as ineffective at colonizing the bladder as were mutants lacking the entire type 1 pili (18). These latter studies lend support to the hypothesis that interference with the interaction of bacterial type 1 adhesin with the high-mannose glycoprotein, either by tying up the high-mannose site or by altering the pili in some way, could provide a useful chemotherapy for these types of infections.

The prior art is deficient in the ability to effectively and consistently treat gram-negative bacterial infections. More specifically, the prior art is deficient in preventing the adhesion of pathogenic bacteria to the mucous membranes of the host cells. The present invention fulfills this long-standing need and desire in the art.

SUMMARY OF THE INVENTION

*Enterobacter cloacae* has been implicated as one of the causative agents in neonatal infection and causes a septicemia thought to be initiated via the gastrointestinal tract. This invention provides a new approach to chemotherapy of infections by gram-negative species in the Enterobacter genus. This approach involves the use of agents that block the attachment of bacteria to intestinal epithelial brush border cells. If the attachment of the bacteria to the host cell surface involves a receptor mediated process, it should be inhibited by substances that block this interaction. Such substances should include compounds that mimic the receptor binding site, as well as antibodies against the receptor binding site (4,20). In addition, compounds that mimic the structure of the ligand being recognized by the receptor should also prevent this interaction. Such a compound could be, for example, infused into the intestinal tract of neonates and patients at high risk to prevent infection.

The adhesion of *Enterobacter cloacae* to intestinal cells was examined to determine the molecular details of the interaction between bacterial pili and cell surface N-linked glycoproteins. Assay conditions were also developed to study the effects of a variety of well-characterized high-mannose oligosaccharides in inhibiting the binding of *Enterobacter cloacae*, or its isolated pili, to HT-29 cell monolayers. This invention demonstrates that pili binding is most effectively and specifically blocked by the addition of $Man_9GlcNAc_2$ glycopeptides, rather than by oligosaccharides containing fewer mannose residues. In addition, binding is enhanced when HT-29 cells are grown in the presence of inhibitors that increase the number (amount) of protein-bound $Man_9(GlcNAc)_2$ structures at the cell surface. Studies using purified pili show that these structures bind in a dose-dependent manner, and this binding is effectively blocked by $Man_9GlcNAc_2$-tyrosinamide, as well as by antibodies directed against the 35 kDa pili subunit.

One object of the present invention is to provide a means to inhibit bacterial adhesion to a host cell membrane using a high-mannose containing oligosaccharide. This treatment would be used in conjunction with a normal course of antibiotic treatment, or in the treatment of multi-drug resistant pathogens.

In an embodiment of the present invention, there is provided a method for the use of $Man_9(GlcNAc)_2$ oligosaccharides as treatment for bacterial infection of *Enterobacter cloacae*, or other Enterobacter species, in an individual in need of such treatment.

In another embodiment of the present invention, there is provided a method for the use of $Man_9(GlcNAc)_2$-tyrosinamide in the treatment of *Enterobacter cloacae* infection, or infection resulting from other Enterobacter species, in an individual in need of such treatment.

In yet another embodiment of the present invention, there is provided a method for the use of $Man_9(GlcNAc)_2$-R, where R can be, but is not limited to, aromatic glycosides, in the treatment of *Enterobacter cloacae* infection, or infection resulting from other Enterobacter species, in an individual in need of such treatment.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

FIG. 6 shows the sequence homologies between the *Enterobacter cloacae* adhesive subunit (i.e., Query) and the FimH protein of *Salmonella typhimurium*. Sequences were compared by the BLAST search.

DETAILED DESCRIPTION OF THE INVENTION

Figure 1:
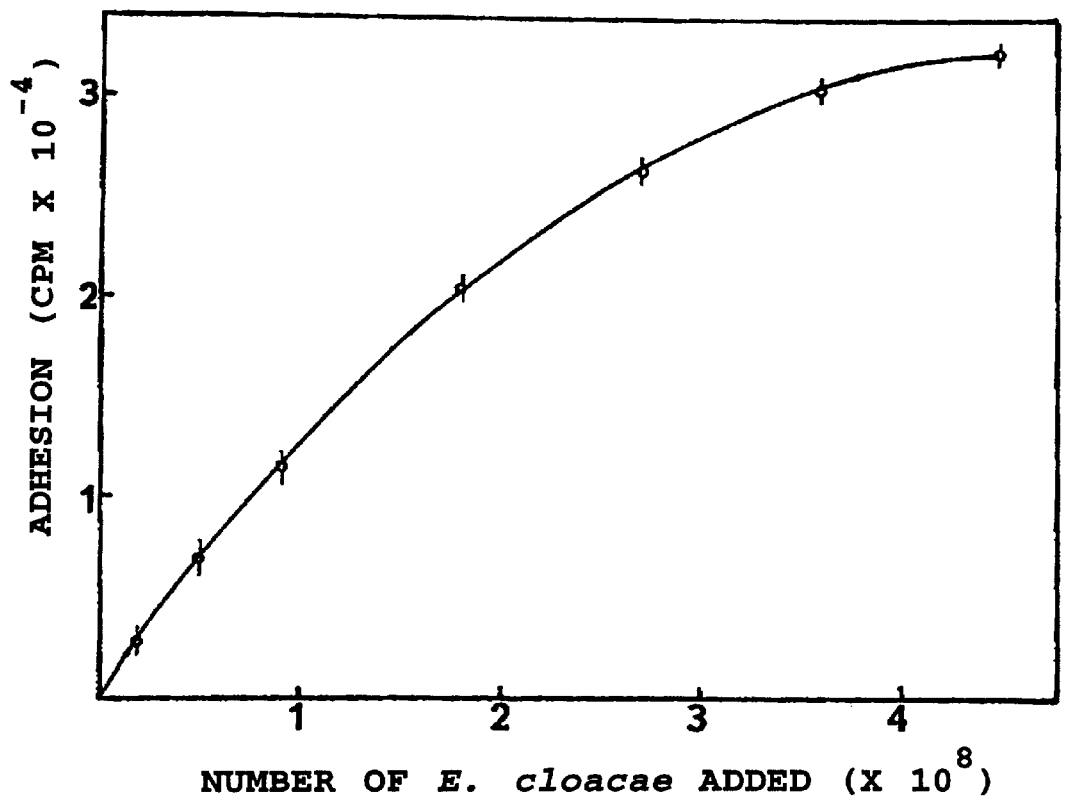
FIG. 1 shows the kinetics of adhesion of [$^3$H]-*Enterobacter cloacae* to HT-29 cell monolayers. Various amounts of the labeled bacterial suspension were added and the number of bacteria bound was determined by scintillation counting.

The present invention is directed toward a method for treatment of bacterial infection by *Enterobacter cloacae* and other Enterobacter species using a high-mannose containing oligosaccharide. The high-mannose containing oligosaccharide binds to the bacterial pili and thereby inhibits adhesion of the bacteria to the glycoproteins on the plasma membrane of the host cell.

It is specifically contemplated that pharmaceutical compositions may be prepared using the novel oligosaccharide of the present invention. In such a case, the pharmaceutical composition comprises a high mannose oligosaccharide of the present invention and a pharmaceutically acceptable carrier. A person having ordinary skill in this art would readily be able to determine, without undue experimentation, the appropriate dosages and routes of administration of the high mannose oligosaccharides of the present invention. When used in vivo for therapy, the high-mannose oligosaccharides of the present invention are administered to the patient or an animal in therapeutically effective amounts, i.e., amounts that effectively inhibit binding by the pathogenic bacteria. It will normally be administered parenterally, preferably intravenously, but other routes of administration will be used as appropriate. The dose and dosage regimen will depend upon the nature of the bacterial infection, the characteristics of the particular inhibitor, e.g., its therapeutic index, the patient, the patient's history and other factors. The amount of the oligosaccharide administered will typically be in the range of about 10 to about 100 mg/kg of patient weight. The schedule will be continued to optimize effectiveness while balanced against negative effects of treatment. See Remington's Pharmaceutical Science, 17th Ed. (1990) Mark Publishing Co., Easton, Pa.; and *Goodman and Gilman's: The Pharmacological Basis of Therapeutics* 8th Ed (1990) Pergamon Press; which are incorporated herein by reference. For parenteral administration, the high mannose oligosaccharides will most typically be formulated in a unit dosage injectable form (solution, suspension, emulsion) in association with a pharmaceutically acceptable parenteral vehicle. Such vehicles are preferably non-toxic and non-therapeutic. Examples of such vehicles are water, saline, Ringer's solution, dextrose solution, and 5% human serum albumin. Nonaqueous vehicles such as fixed oils and ethyl oleate may also be used. Liposomes may be used as carriers. The vehicle may contain minor amounts of additives such as substances that enhance isotonicity and chemical stability, e.g., buffers and preservatives.

The following examples are given for the purpose of illustrating various embodiments of the invention and are not meant to limit the present invention in any fashion:

EXAMPLE 1

Materials

HT-29 cells (ATCC HTB38) were obtained from the American Type Culture Collection. McCoy's 5A medium (modified) and fetal calf serum were purchased from Gibco BRL. *Enterobacter cloacae* was isolated from a patient at Arkansas Children's Hospital. Castanospermine was isolated from the seeds of the tree, *Castanospermum australe*, as previously described (13), and swainsonine from the leaves of the plant, *Astragalus lentiginosus*, as previously reported (25). Kifunensine was supplied by Drs. M. Yamashita and M. Iwani, Fujisawa Pharmaceutical Co., Ibanaki, Japan. Deoxymannojirimycin was purchased from Boehringer Mannheim. [U-$^3$H]-Glucose (2–10 Ci/mmol) was obtained from American Radiolabeled Chemicals, and Concanavalin A, yeast mannan, ovalbumin and jack bean α-mannosidase were from Sigma Chemical Co. All other chemicals were purchased from reliable chemical sources and were of the highest grade available.

EXAMPLE 2
Growth of Mammalian Cells and Bacteria

HT-29 cells were maintained and grown in 75 or 150 $^3$cm flasks in McCoy's 5A modified medium supplemented with 10% inactivated (56° C., 30 min) fetal calf serum. Growth was at 37° C. in a 10% $CO_2$ atmosphere. HT-29 cells were released from flasks with trypsin and plated into 24 well plastic plates in McCoy's medium, and incubated as described above. The same number of cells were added to each well, and this number resulted in a confluent layer within 24 hours. These cultures were used to measure bacterial binding. *Enterobacter cloacae* were grown in Trypticase Soy broth for 24 to 48 hours at 37° C. Cells were harvested by centrifugation, washed with phosphate-buffered saline (PBS) and then resuspended in PBS at a known concentration.

EXAMPLE 3
Radiolabeling of *Enterobacter cloacae*

*Enterobacter cloacae* were grown in 250 ml Erlenmeyer flasks containing 50 ml of Trypticase Soy broth without dextrose, and 100 μCi of [$^3$H]-Glucose were added to the medium. Bacteria were allowed to grow for 48 hours and were harvested by centrifugation. Bacterial pellets were washed repeatedly with PBS until the supernatant liquid was free of radioactivity and radiolabeled bacteria were suspended in PBS at a concentration of $1.8 \times 10^9$ cells/ml (containing 860,000 cpm of radioactivity/ml). This suspension was aliquoted into a number of small tubes and stored in the freezer until used. This bacterial suspension was used throughout the study. There was no detectable loss in viability of the bacteria during this storage procedure.

EXAMPLE 4
Adherence Assay

Bacterial adherence was measured as follows: confluent HT-29 cell monolayers, contained in 24 well plates, were washed two times with PBS. Various amounts of the labeled bacteria, all in the same final volume of buffer, were added to the monolayers and allowed to incubate at 37° C. for 1 hour, with intermittent agitation. At least three wells received each concentration of bacteria. At the end of the incubation, unbound bacteria were removed by aspiration, and the monolayers were washed at least 5 times with PBS. After this thorough washing, the HT-29 cells were released from each well with a trypsin-EDTA mixture and the cell suspension was placed in a scintillation vial. Each well was then washed with another 0.5 ml of water along with scraping with a plastic paddle to remove any firmly attached cells. This second wash was then added to the same vial that contained the first trypsin digest. Ten ml of scintillation fluid were added and radioactivity was determined as a measure of the number of bacteria bound. No binding of bacteria was found to occur to plastic wells that did not contain HT-29 cell monolayers.

EXAMPLE 5
Adherence of *Enterobacter cloacae* to HT-29 Cells and Determination of Sugar Specificity for Bacterial Adherence

*Enterobacter cloacae* bound to the HT-29 cell monolayers as demonstrated in FIG. 1. This binding showed saturation kinetics, and the number of bacteria that were bound increased with increasing numbers of bacteria added to the monolayers. Thus at saturation, $6.7 \times 10^7$ bacteria bound to $1.2 \times 10^6$ HT-29 cells, or an average of about 55 bacteria per animal cell. The number of bacteria bound was calculated based on the specific activity of the bacterial suspension (cpm/bacteria), and was quite reproducible with a variation of about 10% from experiment to experiment. The binding of bacteria to the monolayers was temperature sensitive and was considerably higher at 37° C. than at 5° C. (data not shown). The binding was also proportional to time of incubation, and increased with increasing time up to about 30 minutes. These data are indicative of a receptor mediated process.

Figures 2, 3:
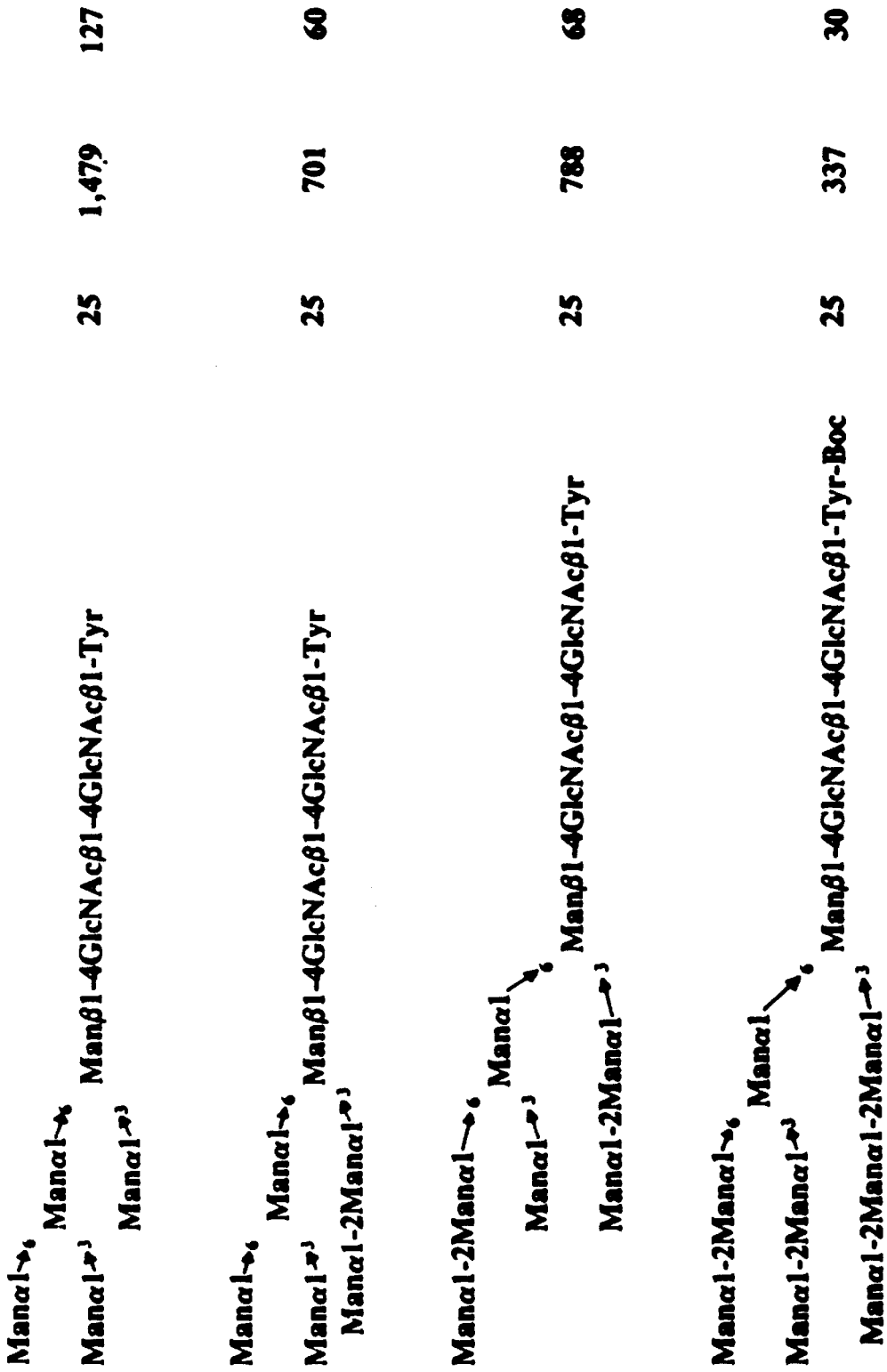
FIG. 3 shows a comparison of inhibition of binding by various well-characterized high-mannose oligosaccharides. Each oligosaccharide was tested at 25 µM concentration to determine its ability to function as an inhibitor. Binding was determined by scintillation counting.

A variety of simple sugars (D-mannose, D-galactose, D-fructose, L-fucose, D-GlcNAc, sialic acid) were tested at various concentrations to determine their ability to block the adhesion of *Enterobacter cloacae* to the HT-29 cells. In addition, p-nitrophenyl-α-D-mannoside and 4-methylumbelliferyl-α-D-mannoside and glycopeptides with various high-mannose or complex types of oligosaccharides were also tested as inhibitors. The structures of the most active of these N-linked oligosaccharides are shown in FIG. 3, and the details of their preparation are presented below. In these experiments, the carbohydrate tested was added to the HT-29 cell monolayer just prior to the addition of the radiolabeled bacterial suspension, in order to best compare its ability to compete with the HT-29 cell glycoproteins. The plates were then incubated and harvested as described above in the adherence assay, and the amount of radioactivity bound to the cell monolayer was determined.

The binding of the labeled bacteria to the cell monolayer was inhibited by adding unlabeled *Enterobacter cloacae*, as well as by adding various simple sugars. Thus, 50% inhibition of binding was observed in the presence of 500 μM D-mannose, 150 μM (-D-methylmannoside, 20 μM p-nitrophenyl-α-D-mannoside or 10 μM 4-methylumbilliferyl-α-D-mannoside (data not shown). Other simple sugars, such as D-glucose, D-galactose, L-fucose, N-acetylglucosamine, N-acetylgalactosamine and sialic acid did not inhibit binding even at 100 mM concentrations. Binding was reversed by adding 5 mM α-methylmannoside or 0.5 mM p-nitrophenyl-α-D-mannoside to the monolayers after the bacteria had bound. Since binding could be inhibited by 80 to 90% at 100 μM methylumbelliferyl-α-mannoside, it seems likely that the *Enterobacter cloacae* binding to HT-29 cells is mostly mediated by type 1 pili.

EXAMPLE 6
Preparation of Various N-linked High-Mannose Oligosaccharide structures as Potential Inhibitors High-mannose oligosaccharides containing 5, 6 and 7 mannose residues were prepared as tyrosinamide oligosaccharides from ovalbumin as described (33). A Man$_9$(GlcNAc)$_2$-tyrosinamide oligosaccharide was prepared from soy bean agglutinin (SBA) as described below. Briefly, soy bean agglutinin (3 g) were purified from untoasted soy flour (1 Kg) according to the method reported by Lis et al (22,23). The N-linked oligosaccharides were released from the reduced and alkylated glycoprotein using N-glycosidase F, and following the formation of a glycosylamine, the oligosaccharides were derivatized with Boc-tyrosine-N-hydroxysuccinimide ester as reported for ovalbumin oligosaccharides (33). The tyrosinamide-oligosaccharides were purified by gel filtration chromatography, and the major oligosaccharide (90% of the total) was resolved to homogeneity on an analytical reverse phase-HPLC column eluted with 0.1% acetic acid and 9% acetonitrile. The oligosaccharides could be detected by their absorption at 280 nm. The major oligosaccharide peak was pooled, dried and characterized by proton NMR which verified the presence of the β-tyrosinamide linkage to a $Man_9(GlcNAc)_2$ oligosaccharide.

EXAMPLE 7
Adherence Involves Recognition of High-Mannose Oligosaccharides

Figure 2:
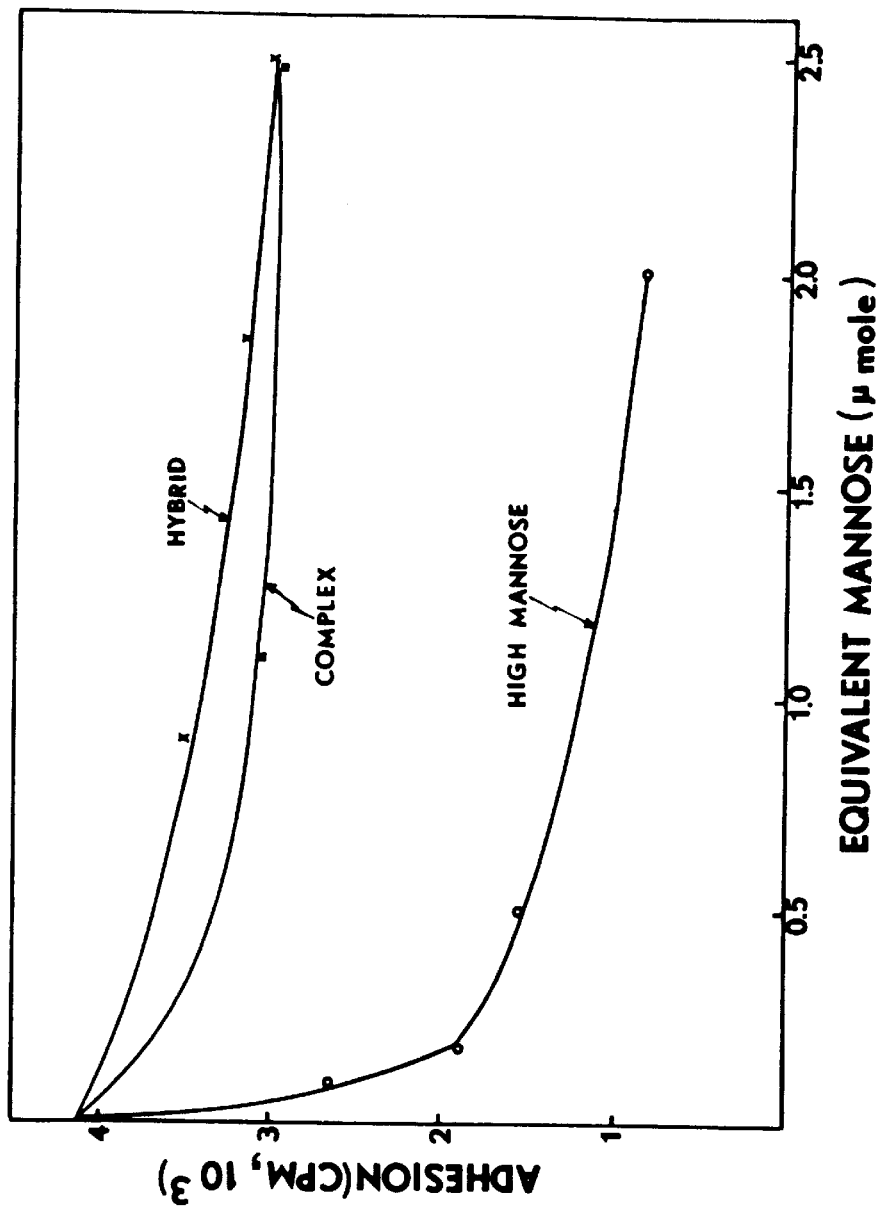
FIG. 2 shows the effect of various oligosaccharide structures on the inhibition of binding of *Enterobacter cloacae* to HT-29 cell monolayers. HT-29 cells were incubated with radiolabeled bacteria in the presence of various amounts of oligosaccharide. The number of radioactive bacteria bound was measured by scintillation counting.

The binding of Enterobacter cloacae to the HT-29 cell monolayers was blocked by a mixture of high mannose oligosaccharides that were isolated by pronase digestion of ovalbumin. The inhibition curve shown in FIG. 2 demonstrates that this mixture caused a 50% inhibition of binding at about 0.1 μmole equivalents of mannose [as measured by the anthrone method (32)]. The figure also shows that complex or hybrid types of oligosaccharides were not effective inhibitors even at high μM concentrations. This data suggests that the receptor molecule on the bacteria recognizes high-mannose oligosaccharides on the HT-29 cell surface.

In order to determine the specificity for high-mannose structures, a series of oligosaccharides that contained 3 to 9 mannose residues, as shown in FIG. 3, were tested at a concentration of 25 μM for their ability to inhibit the binding of Enterobacter cloacae to the HT-29 cell monolayers. The data clearly shows that the $Man_9(GlcNAc)_2$-T was the best inhibitor, while the $Man_7(GlcNAc)_2$-T and $Man_6(GlcNAc)_2$-T could also block adhesion, but less effectively than the $Man_9(GlcNAc)_2$ structure. Table I further substantiates that $Man_9(GlcNAc)_2$ was the best blocking agent, with 50% inhibition occurring at 5 μM concentration. However, those oligosaccharides having fewer mannoses required concentrations of 37.5 μM or higher to cause 50% inhibition. $Man_5(GlcNAc)_2$ or simpler structures were not effective at inhibiting binding even when tested at substantially higher concentrations.

EXAMPLE 8
Effect of Inhibition of N-Linked Oligosaccharide Processing on Bacterial Adhesion As indicated above, N-linked oligosaccharides can be altered by growing eucaryotic cells in the presence of inhibitors of glycoprotein processing (19). A number of compounds are known that inhibit the glycosidases involved in the initial stages of processing (5). Two such compounds, deoxymannojirimycin and kifunensine, inhibit the α-mannosidases that trim the first 4 mannoses from the $Man_9(GlcNAc)_2$ oligosaccharide (7), whereas castanospermine prevents the removal of the glucose residues (5,31). As a result, mannosidase I inhibitors increase the number (i.e., the amount) of $Man_9(GlcNAc)_2$ structures present at the cell surface by effectively preventing their conversion to complex (and hybrid) structures. These inhibitors thus provide valuable tools to determine the in vivo role of high-mannose structures on the adhesion of Enterobacter cloacae.

HT-29 cells were transferred at low density to multiwell plates, and grown in McCoy's medium containing different concentrations of various processing inhibitors. Thus, one 24-well plate was divided into 4 sections, each with 6 wells having the following components: castanospermine at 0, 5, 10, 25, 50 and 100 μg/ml; deoxymannojirimycin at 0, 5, 25, 50, 100 and 200 μg/ml; kifunensine at 0, 2, 5, 10, 25 and 50 μg/ml; swainsonine at 0, 1, 5, 10, 25 and 50 μg/ml. HT-29 cells were allowed to grow to confluency over a period of 4 to 5 days. Once the cells reached confluency, the media was removed by aspiration and the monolayers were washed with PBS. Each well was then challenged with the same number of radioactive bacteria to determine the extent of bacterial adhesion, as described above in the adhesion assay.

The data in Table II show that with kifunensine or deoxymannojirimycin, there was a 50 to 75% increase in the number of radioactive bacteria bound to the monolayers. On the other hand, castanospermine, which prevents the removal of glucose and therefore almost completely blocks any trimming (31), did not cause any significant change in the amount of radioactivity bound. Swainsonine, an inhibitor that acts on mannosidase II and causes an increase in the formation of hybrid types of structures (6), also did not cause any change in the binding of bacteria to the HT-29 cells. These data suggest that the pili recognize $Man_9(GlcNAc)_2$ and this oligosaccharide is the cause of the initial binding of bacteria to the cells.

TABLE I

Effect of Concentration of Various Oligosaccharides on Bacterial Adhesion

| Oligosaccharide Added | Concentration (μM) | Adherence CPM | % of Control |
|---|---|---|---|
| None | — | 1183 | 100 |
| $Man_9GlcNAc_2$-T* | 5 | 660 | 56 |
|  | 15 | 480 | 41 |
|  | 25 | 494 | 42 |
| $Man_7GlcNAc_2$-T | 12.5 | 746 | 63 |
|  | 25 | 721 | 61 |
|  | 37.5 | 466 | 49 |
| $Man_6GlcNAc_2$-T | 12.5 | 856 | 72 |
|  | 25 | 736 | 62 |
|  | 37.5 | 734 | 63 |
| $Man_5GlcNAc_2$-T | 50 | 1518 | 128 |

*Glycopeptides were added to assay mixtures as described. The amount of radiolabeled bacteria adhering to HT-29 monolayers was measured by scintillation counting.

TABLE II

Effect of inhibitors on N-linked glycoprotein processing on the adhesion of E. cloacae to HT-29 cells

| Inhibitor[a] | Concentration (μg/ml) | Adhesion[b] (cpm) | Increase[c] in adhesion (%) |
|---|---|---|---|
| Castanospermine | 0 | 13,857 | — |
|  | 5 | 12,410 | — |
|  | 10 | 13,787 | — |
|  | 25 | 13,973 | — |
|  | 50 | 13,626 | — |
|  | 100 | 14,943 | 8 |
| Swainsonine | 0 | 13,874 | — |
|  | 1 | 15,219 | 10 |
|  | 5 | 14,577 | 5 |
|  | 10 | 15,275 | 11 |
|  | 25 | 13,857 | — |
|  | 50 | 14,965 | 8 |
| Deoxymannojirimycin | 0 | 13,723 | — |
|  | 5 | 18,630 | 36 |
|  | 25 | 20,180 | 47 |
|  | 50 | 20,500 | 49 |
|  | 100 | 21,018 | 53 |

TABLE II-continued

Effect of inhibitors on N-linked glycoprotein processing on the adhesion of *E. cloacae* to HT-29 cells

| Inhibitor[a] | Concentration (μg/ml) | Adhesion[b] (cpm) | Increase[c] in adhesion (%) |
|---|---|---|---|
|  | 200 | 20,548 | 50 |
| Kifunensine | 0 | 13,438 | — |
|  | 2 | 19,033 | 42 |
|  | 5 | 20,161 | 50 |
|  | 10 | 19,257 | 43 |
|  | 25 | 20,414 | 52 |
|  | 50 | 23,442 | 75 |

HT-29 cells were grown in the culture medium in the presence of various concentrations of processing inhibitors. When the cell layer had reached confluency (about 7 days after the last passage), the adhesion assay was performed.
[a]Structures of processing inhibitors are given in FIG. 6.
[b]Average of three sets of experiments.
[c]Expressed in percent relative to the control.

EXAMPLE 9
Isolation and Characterization of the Adhesin Subunit of *Enterobacter cloacae* Pili The isolation of pili from *Enterobacter cloacae* followed described methods (14). Cells were grown in Trypticase Soy broth and 6 liters of cells were harvested by centrifugation and resuspended in 250 ml of 5 mM Tris-HCl buffer, pH 7.4, containing 1 M NaCl. The cooled (4° C.) cell suspension was homogenized for 4 minutes in a Waring blender, then cooled and homogenized again. This homogenization procedure was repeated 4 times. The bacteria were removed by centrifugation, resuspended in buffer and subjected to another homogenization procedure. The supernatant liquids from the two homogenizations, containing the released pili, were combined, and solid ammonium sulfate was added slowly with stirring in an ice bath to reach a concentration of 10% (wt/vol). The mixture was allowed to stand for 60 min at 4° C., and the precipitate was removed by centrifugation and discarded. Solid ammonium sulfate was slowly added with stirring to reach a concentration of 30% (wt/vol), and the mixture was allowed to stand for 4 hours at 4° C. The precipitate resulting from this treatment contained the pili, and this precipitate was collected by centrifugation and resuspended in sterile distilled water. This pili solution was subjected to cesium chloride density gradient centrifugation (42% wt/vol) for 8 hours at 100,000 xg, and the dense white band of pili was collected, diluted 1:5 in sterile distilled water and pelleted in a fixed angle rotor at 100,000 xg for 2 hours. The gelatinous pili pellet was resuspended in sterile distilled water and stored at 4° C.

The pili preparations were frequently contaminated with outer membrane proteins such as the 35 kDa protein of omp A. These proteins could be detected by Western blot analysis, using antibody against omp A, supplied by Dr. H. Nakaido. The contaminated pili were suspended in 4% SDS in 10 mM Tris buffer, pH 8, containing 15 mM dithiothreitol and stirred for 1 hour at room temperature. Insoluble pili were sedimented by centrifugation at 25,000 xg for 1 hour at 10° C. This pellet was resuspended in SDS-dithiothreitol buffer as above, stirred and subjected to centrifugation to reisolate the pili. This procedure was repeated several more times and effectively removed most of the outer membrane proteins (12).

Figure 4:
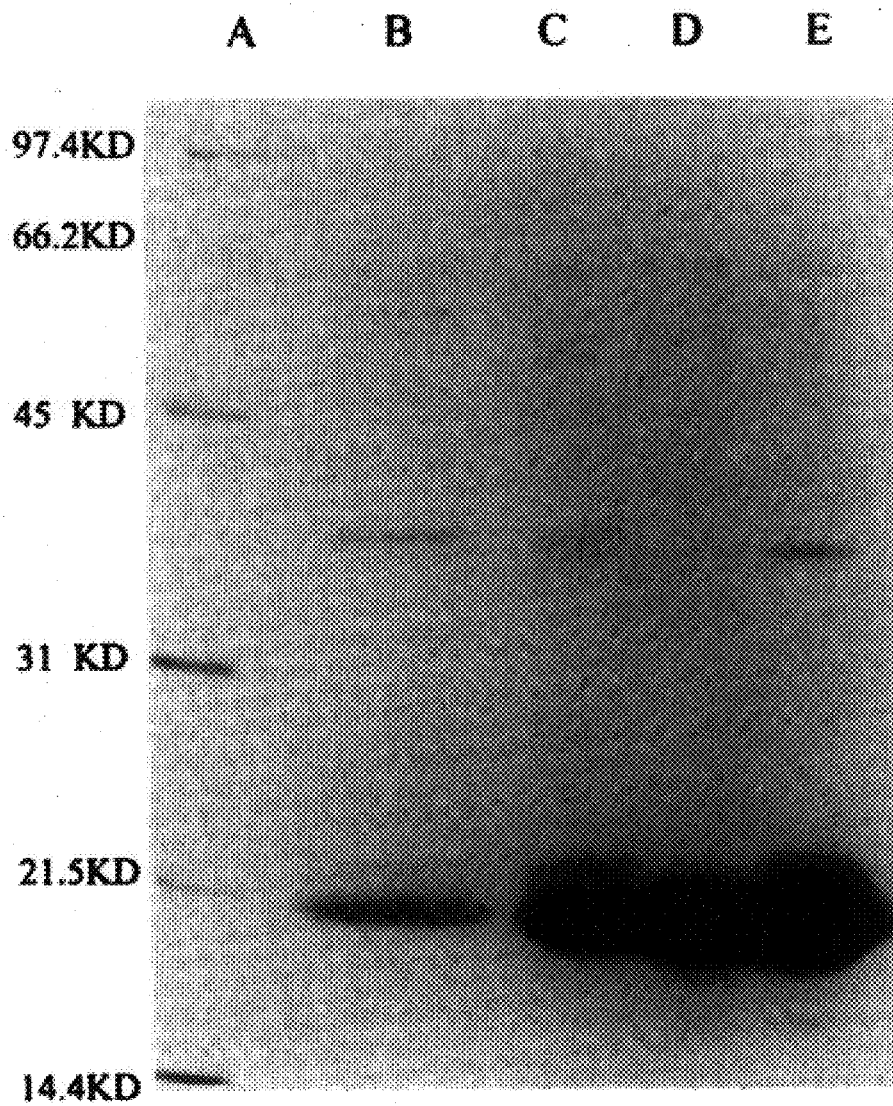
FIG. 4 shows SDS gel electrophoresis of pili at various stages of purification. Lanes shown are as follows: A. Molecular weight standards of 97.4, 66.2, 45, 31, 21.5 and 14.4 kDa; B. Supernatant fraction after homogenization and low-speed centrifugation; C. Precipitate obtained by ammonium sulfate fractionation of above supernatant fraction; D. Pili fraction isolated by cesium cholride density gradient fractionation; E. Highly purified pili after removal of membrane proteins with Tris-HCl buffer. Proteins were detected by Coomassie Blue staining.
Figure 5:
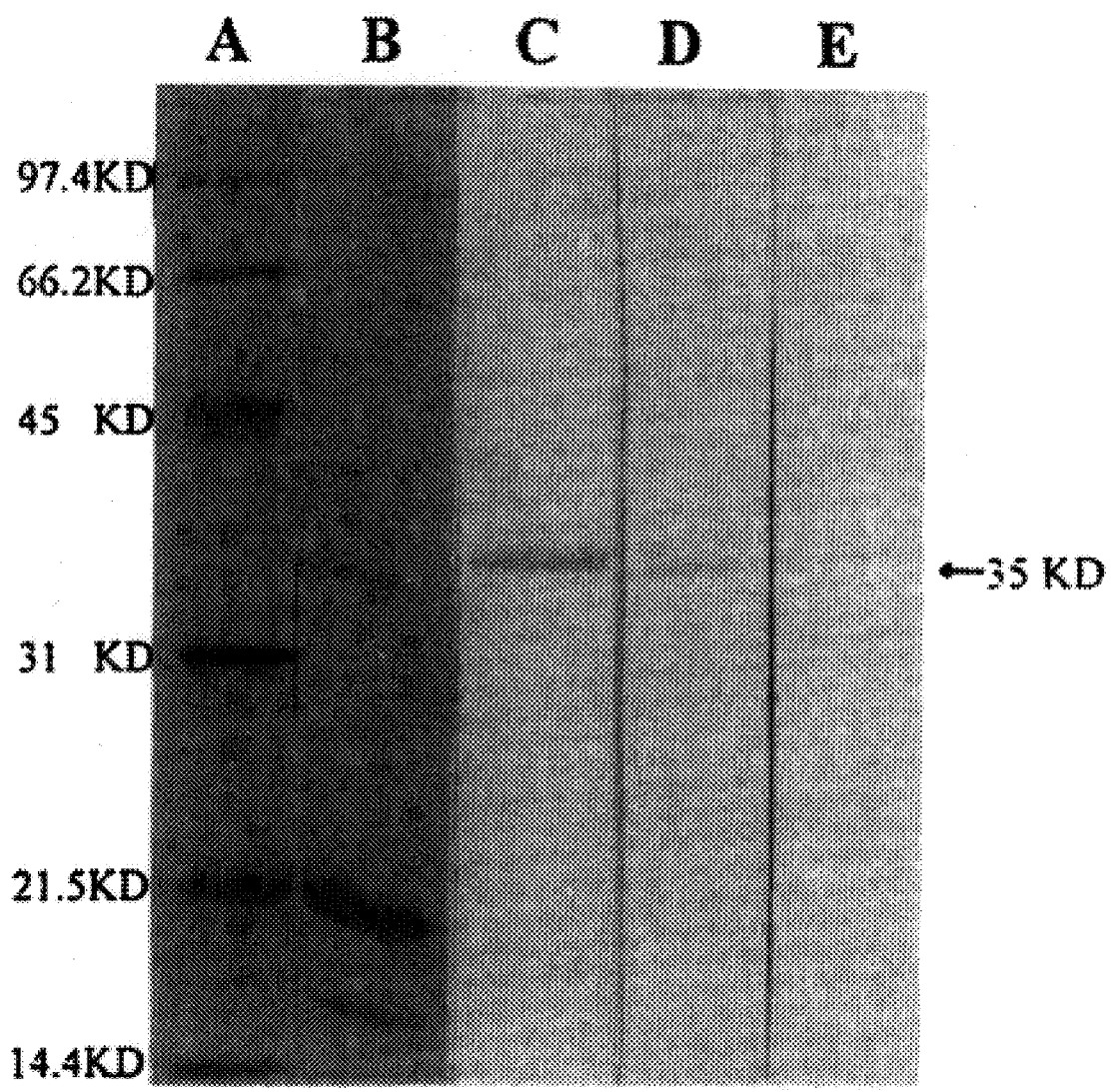
FIG. 5 shows the detection of pili adhesive subunit by binding of α-mannosylated-biotinylated-albumin. Lanes are as follows: A. Molecular weight standards as in FIG. 4; B. Isolated pili after transfer to nitrocellulose membranes and detection with Amido Black; C. Modified Western blot using an α-mannosylated-biotinylated-albumin, followed by an avidin-horseradish peroxidase conjugate and then visualization with 4-chloro-napthol according to the manufacturer's directions; D. Reaction system as in C, but incubated in the presence of 50 mM α-D-glucose; E. Reaction system as in C and D, but incubated in the presence of 50 mM α-D-mannose.

The protein profiles of each fraction upon SDS-PAGE is shown in FIG. 4. *Enterobacter cloacae* pili were isolated by centrifugation (FIG. 4, lane B), and purified by ammonium sulfate precipitation (lane C) and then density gradient centrifugation (lane D). SDS gel electrophoresis of the pili under reducing conditions showed a major subunit of 20 kDa, and minor subunits of 35, 17 and 15 kDa. Since the binding of *Enterobacter cloacae* to HT-29 cells is blocked by high-mannose structures, it was likely that the pili were type 1 pili which should bind to mannose-containing structures. Thus, purified pili were subjected to 12% SDS-PAGE, and the resulting protein bands were transferred to nitrocellulose membranes. After washing the membranes to remove SDS, and incubating them with PBS containing 5% bovine serum albumin, they were incubated for 2 hours at room temperature with a mannosylated-albumin that contained a biotin tag. Some incubations also contained 50 mM D-mannose or 50 mM D-glucose. The binding subunit was identified by its reaction with an albumin analog that contained covalently-bound mannose, as well as a biotin tag. FIG. 5, lane C, shows that only the 35 kDa band became labeled with this tag, and this labeling was inhibited by adding 50 mM D-mannose (lane E), but not 50 mM D-glucose (lane D), to these incubations. Lane B in FIG. 5 is the nitrocellulose membrane of the transferred pili proteins stained with Amido black. The data in this figure suggest that the 35 kDa protein is the adhesive subunit that recognizes $Man_9(GlcNAc)_2$ structures.

The 35 kDa pili subunit was transferred to PVDF membranes and subjected to Endo lys C digestion, isolation of the peptides by HPLC, and amino acid sequencing of several of these peptides. Isolation of peptides and amino acid sequencing were done at the Harvard Microchemistry Facility, Cambridge, Mass. FIG. 6 shows the sequences of several of these peptides compared to sequences of the FimH protein of *Salmonella typhimurium*. One peptide of 15 amino acids showed 85% identity to FimH, while a 26 amino acid sequence showed 69% identity, and another 16 amino acid peptide showed 68% identity. This very strong similarity between these proteins is additional evidence that the 35 kDa protein from *Enterobacter cloacae* is the mannose-binding subunit of this pili.

Figure 7A:
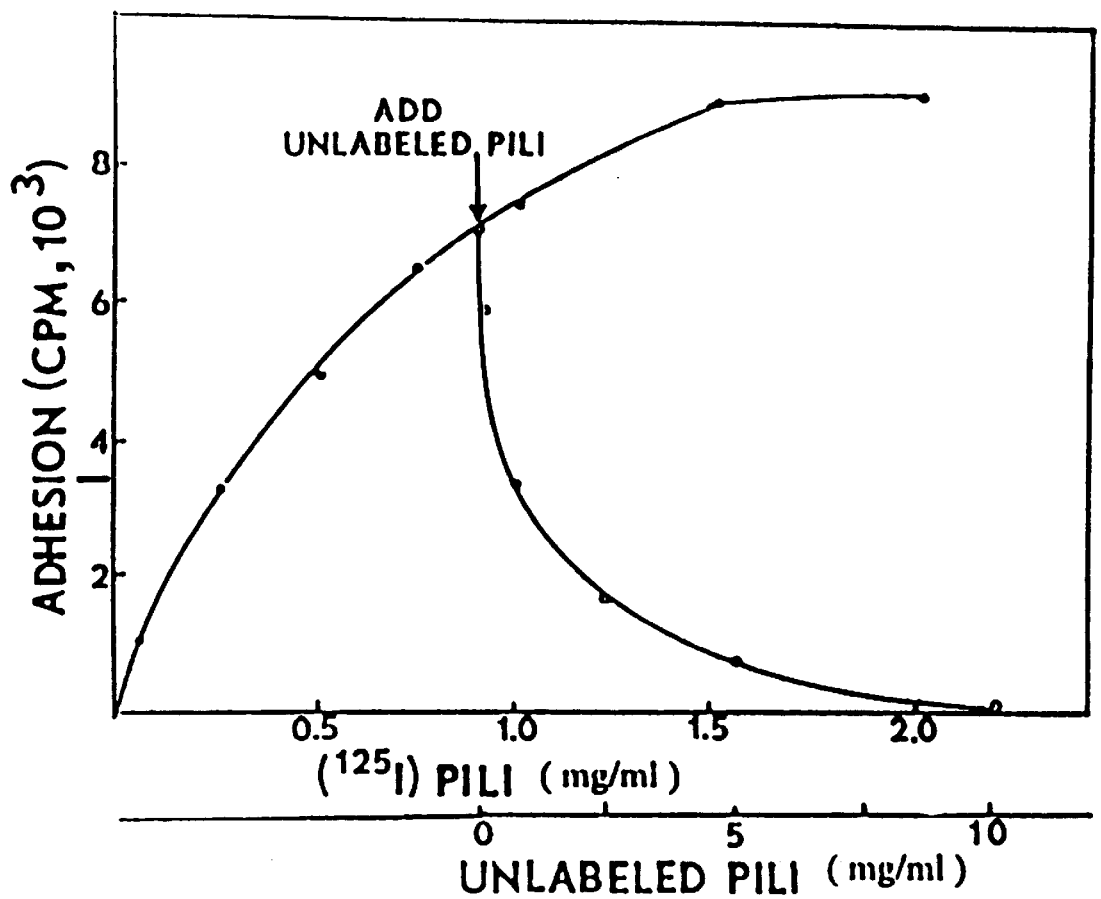
FIG. 7 shows the effect of pili concentration on binding to HT-29 cell monolayers and inhibition by Man$_9$(GlcNAc)$_2$-T oligosaccharide. Various amounts of radiolabeled pili were added to monolayers and the extent of binding was determined. Pili were then mixed with increasing amounts of the Man$_9$(GlcNAc)$_2$-T (o---o), or Man$_5$(GlcNAc)$_2$-T (•---•) and the mixtures were added to HT-29 cells. The amount of pili bound was determined by scintillation counting.
(FIG. 7B)
Figure 7B:
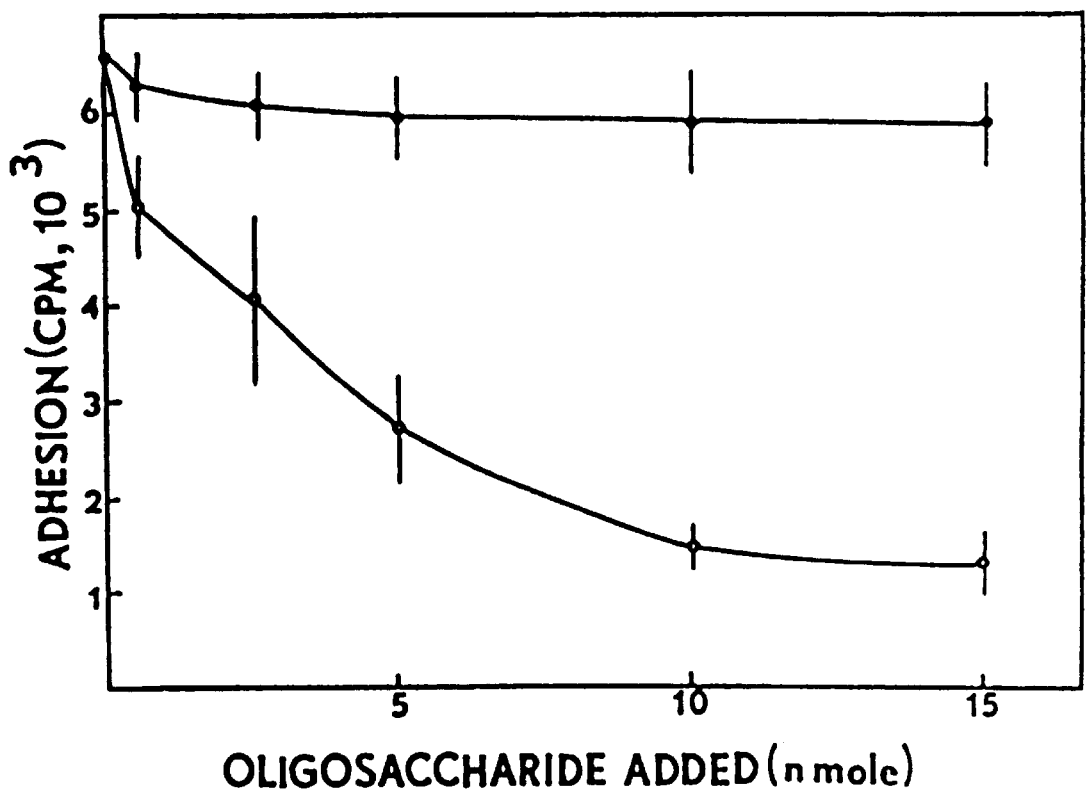

The purified pili were labeled with $^{125}I$, and tested for their ability to bind to HT-29 cells. 100 μg of pili were labeled with $^{125}I$ using N-chloro-benzenesulfonamide-derivatized polysterene beads (Iodo-beads) (24) and then unlabeled pili were added to give a final protein concentration of 2 mg/ml. FIG. 7A shows that the pili bound in a concentration-dependent manner, and showed saturation kinetics. In addition, this binding was blocked in a dose-dependent manner by the addition of increasing amounts of unlabeled pili. The binding of radioactive pili was also inhibited by the addition of increasing amounts of $Man_9(GlcNAc)_2$-T as shown in FIG. 7B, with 50% inhibition occurring at 5 nM concentration. However, $Man_5(GlcNAc)_2$ did not inhibit, nor did other smaller mannose-containing oligosaccharides. These results are similar to those with the intact bacteria, and strongly suggest that the 35 kDa protein is the pili adhesin.

Antibody against the purified adhesin subunit (i.e., 35 kDa band) was raised in a rabbit using standard methods of preparation. Briefly, 100 μg of protein were mixed with Freunds complete adjuvant and injected into a rabbit. Four weeks later another injection of 100 μg of the pili adhesin, mixed with Freunds incomplete adjuvant, was given to the animal. A blood sample taken after two weeks showed a good antibody titer, and the animal was bled for antibody isolation after four weeks. The IgG fraction was purified from the immune serum by ammonium sulfate fractionation (0 to 33% saturation), followed by gradient elution from DEAE-Sephadex. The IgG fraction was concentrated, dialyzed, aliquoted into small tubes and stored at −80° C.

Figure 8:
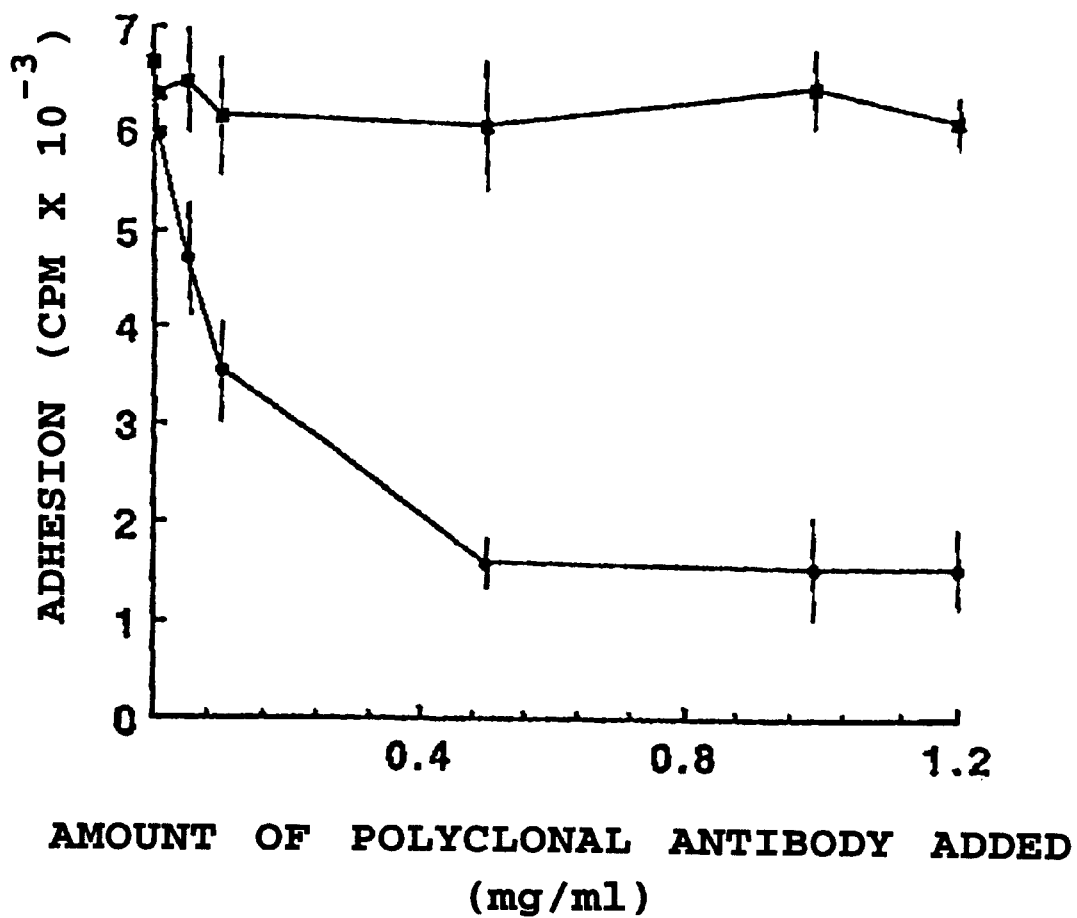
FIG. 8 shows the inhibition of pili binding to HT-29 cells by antipili antibody. Radiolabeled pili were incubated with partially purified IgG prepared against the isolated 35 kDa pili subunit (•---•), or with nonspecific rabbit antibody (≈---≈). After an incubation of 30 minutes at 37° C., the mixtures were added to HT-29 cells and the number of pili bound was determined by scintillation counting.

This IgG was tested for its ability to block the adhesion of the pili subunit, or the intact bacteria, to HT-29 cell monolayers. FIG. 8 shows that this antibody was quite effective in inhibiting pili binding, whereas nonspecific serum was ineffective. Similar results were obtained when binding of intact bacteria was examined in the presence of anti-pili IgG (data not shown). Binding of the 35 kDa protein was also blocked by anti-pili IgG. In studies with punches of fetal rabbit small intestine, radiolabeled *Enterobacter cloacae* or the isolated $^{125}$I-pili showed specific and saturatable binding to these tissue slices, suggesting that this interaction is a naturally and physiologically significant process.

EXAMPLE 10

Summary

Using both well-characterized and natural N-linked oligosaccharides, having from 3–9 mannose residues, as inhibitors of bacterial or pili adhesion to HT-29 cells, it was established that the *Enterobacter cloacae* adhesin preferred the $Man_9(GlcNAc)_2$ structure over $Man_7(GlcNAc)_2$, or smaller oligomers. In addition, blocking the natural processing of N-linked oligosaccharides in the HT-29 cells with specific inhibitors caused an increase in the number of $Man_9(GlcNAc)_2$ structures on the HT-29 cell surface, and also resulted in a considerable increase in the number of bacteria that bound to these cells.

In addition to the recognition of the oligosaccharide by type 1 pili, these lectins may also have a hydrophobic region that interacts with a hydrophobic site(s) on the membrane glycoprotein of the animal cells. These studies with the *Enterobacter cloacae* adhesin have shown the same phenomenon, with methylumbelliferyl-α-mannoside being the most effective of the simple mannosides as an inhibitor. These studies suggest that the $Man_9(GlcNAc)_2$ oligosaccharide structure may be a useful anti-adhesin agent in animals. The following references were cited herein:

1. Acolet, D. et al. 1994. J. Hosp. Infect. 28:273–286.
2. Beachy, E. H. 1981. J. Infect. Dis. 143:325–345.
3. Cleeg, S. et al. 1985. Infect. Immun. 50, 338–340.
4. Eden, C. S. et al. 1990. Curr. Top. Microbiol. Immunol. 151:167–184.
5. Elbein, A. D. 1991. FASEB J. 5:3055–3063.
6. Elbein, A. D. et al. 1981. Proc. Natl. Acad. Sci. USA 78:7393–7397.
7. Elbein, A. D. et al. 1990. J. Biol. Chem. 265:15599–15605.
8. Firon, N. et al. 1987. Infect. Immun. 55:472–476.
9. Firon, N. et al. 1984. Infect. Immun. 43:1088–1090.
10. Gallagher, 1990. Reviews of Infectious Dis. 12:808–812.
11. Gladstone, et al. 1990. Pediatr. Infect. Dis. J. 9:818–825.
12. Hanson, M. S. et al. 1988. J. Bact. 170:3350–3358.
13. Hohenschutz, et al. 1981. Phytochemistry 20:811–814.
14. Hornick, D. B. et al. 1991. J. Clin. Microbiol. 29:1795–1800.
15. Husser, M. F. et al. 1990. Pediatr. Infect. Dis. J. 9:509–512.
16. Jones, et al. 1995. Proc. Natl. Acad. Sci. 92:2081–2085.
17. Karpuch, J. et al. 1983. Isreali J. Med. Sci. 19:963–966.
18. Keith, B. R. et al. 1986. Infect. Immun. 53:693–696.
19. Kornfeld, R., and S. Kornfeld. 1985. Annu. Rev. Biochem. 54:631–664.
20. Krogfelt, K. A. 1991. Rev. Infect. Dis. 13:721–735.
21. Krogfelt, K. A. et al. 1990. Infect.Immun. 58:1995–1998.
22. Lis, H., and N. Sharon. 1978. J. Biol. Chem. 253:3468–3476.
23. Lis, H. et al. 1966. J. Biol. Chem. 241:684–689.
24. Markwell, M. A. 1982. Anal. Biochem. 125:427–432.
25. Molyneux, R. J., and J. P. James. 1982. Science 216:190–191.
26. Nesser, J-R. et al. 1986. Infect. Immun. 52:428–436.
27. Ofek, I., and R. J. Doyle. 1984. Bacterial adhesion to cells and tissues. Chapman and Hall, NY.
28. Ofek, I. et al. 1981. Infect. Immun. 34:708–711.
29. Ofek, I., and N. Sharon. 1990. Curr. Top. Microbiol. Immunol. 151:91–113.
30. Orndorff, and S. Falkow. 1983. J. Bacteriol. 159:736–744.
31. Pan, Y. T. et al. 1981. Biochemistry 22:3975–3984.
32. Seifter, et al. 1950. Arch. Biochem. Biophys. 25:191–200.
33. Silva, et al. 1995. Arch. Biochem. Biophys. 318:465–475.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

---

What is claimed is:

1. A method of inhibiting binding of bacteria to a cell, comprising the steps of contacting said cell with a high-mannose oligosaccharide, said oligosaccharide having more than 6 mannose residues.

2. The method of claim 1, wherein said bacteria are gram-negative.

3. The method of claim 1, wherein said bacteria are *Enterobacter cloacae*.

4. The method of claim 1, wherein the high-mannose oligosaccharide is selected from the group consisting of $Man_9(N\text{-acetylglucosamine})_2$ and $Man_7(N\text{-acetylglucosamine})_2$.

5. The method of claim 1, wherein the high-mannose oligosaccharide is $Man_9(N\text{-acetylglucosamine})_2\text{-tyrosinamide}$.

6. The method of claim 1, wherein the high-mannose oligosaccharide contacts the cells in a concentration from about 0.5 $\mu M$ to about 50 $\mu M$.

7. The method of claim 1, further comprising the steps of contacting said cell with a mannosidase inhibitor.

8. The method of claim 7, wherein said mannosidase inhibitor is selected from the group consisting of mannosidase II inhibitors, deoxymannojirimycin, and kifunensine.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 16
      (B) TYPE: amino acids

```
        (C) STRANDEDNESS:
        (D) TOPOLOGY:  linear (ii) MOLECULE TYPE:
        (A) DESCRIPTION:  peptide (iii) HYPOTHETICAL:  no (iv) ANTI-SENSE:  no (v) FRAGMENT TYPE:  internal (vi) ORIGINAL SOURCE:
        (A) ORGANISM:  Enterobacter cloacae (vii) IMMEDIATE SOURCE:

(viii) POSITION IN GENOME:

(ix) FEATURE:

(x) PUBLICATION INFORMATION:

(xi) SEQUENCE DESCRIPTION:  SEQ ID NO:   1:

Asp Ile Ser Tyr Asp Leu Ser Asn Val Phe Asn Ser Ser Asn Asn
              5                  10                  15

Lys (2) INFORMATION FOR SEQ ID NO:2:

(i) SEQUENCE CHARACTERISTICS:
        (A) LENGTH:  16
        (B) TYPE:  amino acids
        (C) STRANDEDNESS:
        (D) TOPOLOGY:  linear (ii) MOLECULE TYPE:
        (A) DESCRIPTION:  protein (iii) HYPOTHETICAL:  no (iv) ANTI-SENSE:  no (v) FRAGMENT TYPE:  internal (vi) ORIGINAL SOURCE:
        (A) ORGANISM:  Salmonella typhimurium (vii) IMMEDIATE SOURCE:

(viii) POSITION IN GENOME:

(ix) FEATURE:

(x) PUBLICATION INFORMATION:

(xi) SEQUENCE DESCRIPTION:  SEQ ID NO:   2:

Asp Ile Phe Tyr Asp Leu Ser Asp Val Phe Thr Ser Gly Asn Asn
              5                  10                  15

Gln (2) INFORMATION FOR SEQ ID NO:3:

(i) SEQUENCE CHARACTERISTICS:
        (A) LENGTH:  26
        (B) TYPE:  amino acids
        (C) STRANDEDNESS:
        (D) TOPOLOGY:  linear (ii) MOLECULE TYPE:
        (A) DESCRIPTION:  peptide (iii) HYPOTHETICAL:  no
```

(iv) ANTI-SENSE:  no (v) FRAGMENT TYPE:  internal (vi) ORIGINAL SOURCE:
            (A) ORGANISM:  Enterobacter cloacae (vii) IMMEDIATE SOURCE:

(viii) POSITION IN GENOME:

(ix) FEATURE:

(x) PUBLICATION INFORMATION:

(xi) SEQUENCE DESCRIPTION:  SEQ ID NO:   3:

Ile Pro Phe Arg Leu Asp Asp Ser Ala Gln Ala Gln Val Gly Ile
                 5                  10                  15

Arg Val Trp Pro Val Ser Ile Thr Gly Asn Lys
                20                  25

(2) INFORMATION FOR SEQ ID NO:4:

(i) SEQUENCE CHARACTERISTICS:
            (A) LENGTH:  26
            (B) TYPE:  amino acids
            (C) STRANDEDNESS:
            (D) TOPOLOGY:  linear (ii) MOLECULE TYPE:
            (A) DESCRIPTION:  protein (iii) HYPOTHETICAL:  no (iv) ANTI-SENSE:  no (v) FRAGMENT TYPE:  internal (vi) ORIGINAL SOURCE:
            (A) ORGANISM:  Salmonella typhimirium (vii) IMMEDIATE SOURCE:

(viii) POSITION IN GENOME:

(ix) FEATURE:

(x) PUBLICATION INFORMATION:

(xi) SEQUENCE DESCRIPTION:  SEQ ID NO:   4:

Ile Pro Phe His Leu Asp Asp Asn Ala Ala Ala Arg Val Gly Ile
                 5                  10                  15

Arg Ala Trp Pro Ile Ser Val Thr Gly Ile Lys
                20                  26

(2) INFORMATION FOR SEQ ID NO:5:

(i) SEQUENCE CHARACTERISTICS:
            (A) LENGTH:  15
            (B) TYPE:  amino acids
            (C) STRANDEDNESS:
            (D) TOPOLOGY:  linear (ii) MOLECULE TYPE:
            (A) DESCRIPTION:  peptide (iii) HYPOTHETICAL:  no (iv) ANTI-SENSE:  no (v) FRAGMENT TYPE:  internal (vi) ORIGINAL SOURCE:
            (A) ORGANISM:  Enterobacter cloacae

```
        (vii) IMMEDIATE SOURCE:

(viii) POSITION IN GENOME:

(ix) FEATURE:

(x) PUBLICATION INFORMATION:

(xi) SEQUENCE DESCRIPTION:  SEQ ID NO:   5:
Ala Glu Gly Arg Phe Thr Ser Arg Gly Tyr Leu Arg Val Asp Tyr
                 5                  10                  15

(2) INFORMATION FOR SEQ ID NO:6:

(i) SEQUENCE CHARACTERISTICS:
              (A) LENGTH:  15
              (B) TYPE:  amino acids
              (C) STRANDEDNESS:
              (D) TOPOLOGY:  linear (ii) MOLECULE TYPE:
              (A) DESCRIPTION:  protein (iii) HYPOTHETICAL:  no (iv) ANTI-SENSE:  no (v) FRAGMENT TYPE:  internal (vi) ORIGINAL SOURCE:
              (A) ORGANISM:  Salmonella typhimirium (vii) IMMEDIATE SOURCE:

(viii) POSITION IN GENOME:

(ix) FEATURE:

(x) PUBLICATION INFORMATION:

(xi) SEQUENCE DESCRIPTION:  SEQ ID NO:   6:
Ala Glu Gly Pro Phe Thr Ala Arg Gly Tyr Leu Arg Val Asp Tyr
                 5                  10                  15
```